US00PP36735P2

(12) United States Plant Patent
Jan Kraan

(10) Patent No.: US PP36,735 P2
(45) Date of Patent: Jun. 10, 2025

(54) ***HYDRANGEA* PLANT NAMED 'Bokomabo'**

(50) Latin Name: *Hydrangea paniculata*
Varietal Denomination: Bokomabo

(71) Applicant: Kees Jan Kraan, Alphen aan den Rijn (NL)

(72) Inventor: Kees Jan Kraan, Alphen aan den Rijn (NL)

(73) Assignees: BOOT & CO BOOMKWEKERIJEN BV, Boskoop (NL), part interest; KOLSTER HOLDING B.V., Boskoop (NL), part interest ( * ) Notice: Subject to any disclaimer, the term of this patent is extended or adjusted under 35 U.S.C. 154(b) by 0 days.

(21) Appl. No.: 18/948,647

(22) Filed: Nov. 15, 2024

(51) Int. Cl.
*A01H 5/00* (2018.01)
*A01H 6/48* (2018.01)

(52) U.S. Cl.
USPC ..... Plt./250
CPC ..... *A01H 6/48* (2018.05)

(58) Field of Classification Search
USPC ..... Plt./250
CPC ..... A01H 5/00
See application file for complete search history.

*Primary Examiner* — Kent L Bell
(74) *Attorney, Agent, or Firm* — Penny J. Aguirre

(57) ABSTRACT

A new cultivar of *Hydrangea paniculata* plant named 'Bokomabo' that is characterized by its moderately vigorous growth habit, its compact plant habit, its sturdy and healthy foliage, its sterile flower sepals that are white in color and change to dark red-purple to grey-purple after flowering, its ovate to conical shaped inflorescences, and its inflorescences that are not very dense and consist of both fertile and sterile flowers.

4 Drawing Sheets

Botanical classification: *Hydrangea paniculata.*
Varietal denomination: 'Bokomabo'.

BACKGROUND OF THE INVENTION

The present invention relates to a new and distinct cultivar of *Hydrangea paniculata* and will be referred to hereafter by its cultivar name, 'Bokomabo'. 'Bokomabo' represents a new panicle *Hydrangea*, a perennial shrub grown for use as a landscape plant.

'Bokomabo' was derived from an ongoing breeding program conducted by the Inventor in Boskoop, The Netherlands. The goal of the breeding program is to develop new cultivars of *Hydrangea paniculata* with novel characteristics.

The new cultivar originated as a seedling that arose from seed planted from open pollination of an unnamed and unpatented plant of *Hydrangea paniculata* in July of 2012. The male parent is therefore unknown. 'Bokomabo' was selected as a single unique plant in July of 2020 from the resulting seedlings.

Asexual propagation of the new cultivar was first accomplished by softwood stem cuttings by the Inventor in Boskoop, The Netherlands in July of 2020. Asexual propagation by softwood stem cuttings has determined that the characteristics of the new cultivar are stable and are reproduced true to type in successive generations.

SUMMARY OF THE INVENTION

The following traits have been repeatedly observed and represent the characteristics of the new cultivar. These attributes in combination distinguish 'Bokomabo' as a unique cultivar of *Hydrangea.*

1. 'Bokomabo' exhibits a moderately vigorous growth habit.
2. 'Bokomabo' exhibits a compact plant habit.
3. 'Bokomabo' exhibits sturdy and healthy foliage.
4. 'Bokomabo' exhibits sterile flower sepals that are white in color and change to dark red-purple to grey-purple after flowering.
5. 'Bokomabo' exhibits ovate to conical shaped inflorescences.
6. 'Bokomabo' exhibits inflorescences that are not very dense and consist of both fertile and sterile flowers.

The female parent plant of 'Bokomabo' differs from 'Bokomabo' in having weaker, longer stems, a more vigorous growth habit, and sterile flower sepals that change to green and pink after opening. 'Bokomabo' can be most closely compared to the *Hydrangea paniculata* cultivars 'Bokomaho' (U.S. Plant Pat. No. 33,496) and 'Bokomapishad' (U.S. Plant Pat. No. 36,068). 'Bokomaho' is similar to 'Bokomabo' in having a compact plant habit and inflorescences with white sterile flower sepals. 'Bokomaho' differs from 'Bokomabo' in having a more compact plant habit, greater flowering as a one-year-old plant, and sterile flower sepals that change to yellow-green and slightly pink in color after flowering. 'Bokomapishad' is similar to 'Bokomabo' in having a compact plant shape and similar sterile flower sepal color after flowering. 'Bokomapishad' differs from 'Bokomabo' in having inflorescences that have more sterile flowers to cover the fertile flowers, a more vigorous and stronger growing habit that results in longer branches, and inflorescences that are larger in size.

STATEMENT REGARDING PRIOR DISCLOSURES BY THE INVENTOR

The Applicant asserts that no publications or advertisements relating to sales, offers for sale, or public distribution occurred more than one year prior to the effective filing date of this application. Any information about the claimed plant would have been obtained from a direct or indirect disclosure from the Inventor. The Applicant claims a prior art exemption under 35 U.S.C. 102(b)(1) for disclosures and/or sales that fall within a one-year grace period to the filing date. Disclosures include website listings by Plants Nouveau and Bloomin' Easy Plants.

BRIEF DESCRIPTION OF THE DRAWINGS

The accompanying color photographs illustrate the overall appearance and distinct characteristics of the new *Hydrangea*. The photograph were taken of a 3-year-old plant of 'Bokomabo' as grown in 19-cm containers in Boskoop, The Netherlands.

The photograph in FIG. 1 provides a side view of 'Bokomabo' in bloom.

Figure 1:
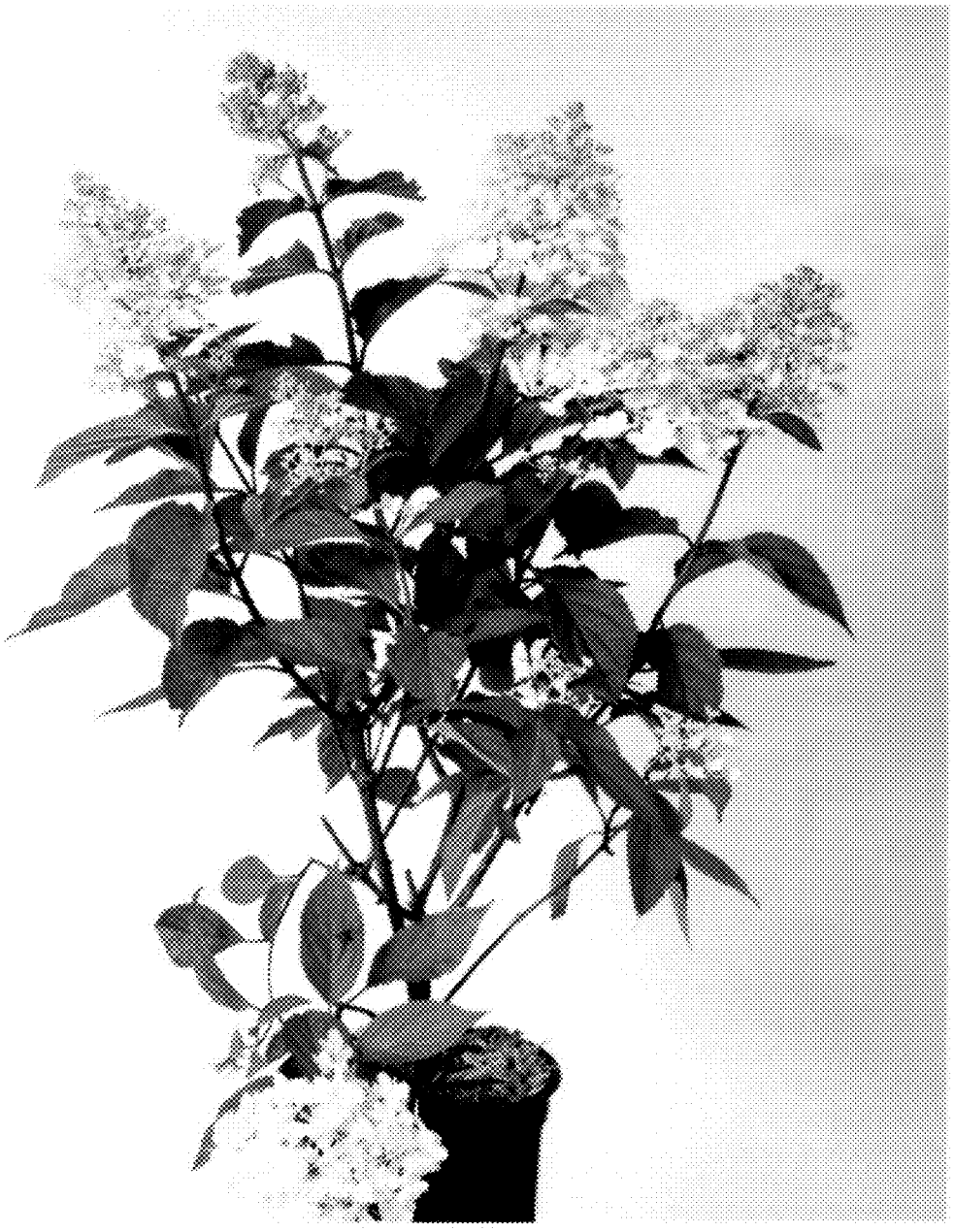
Figure 2:
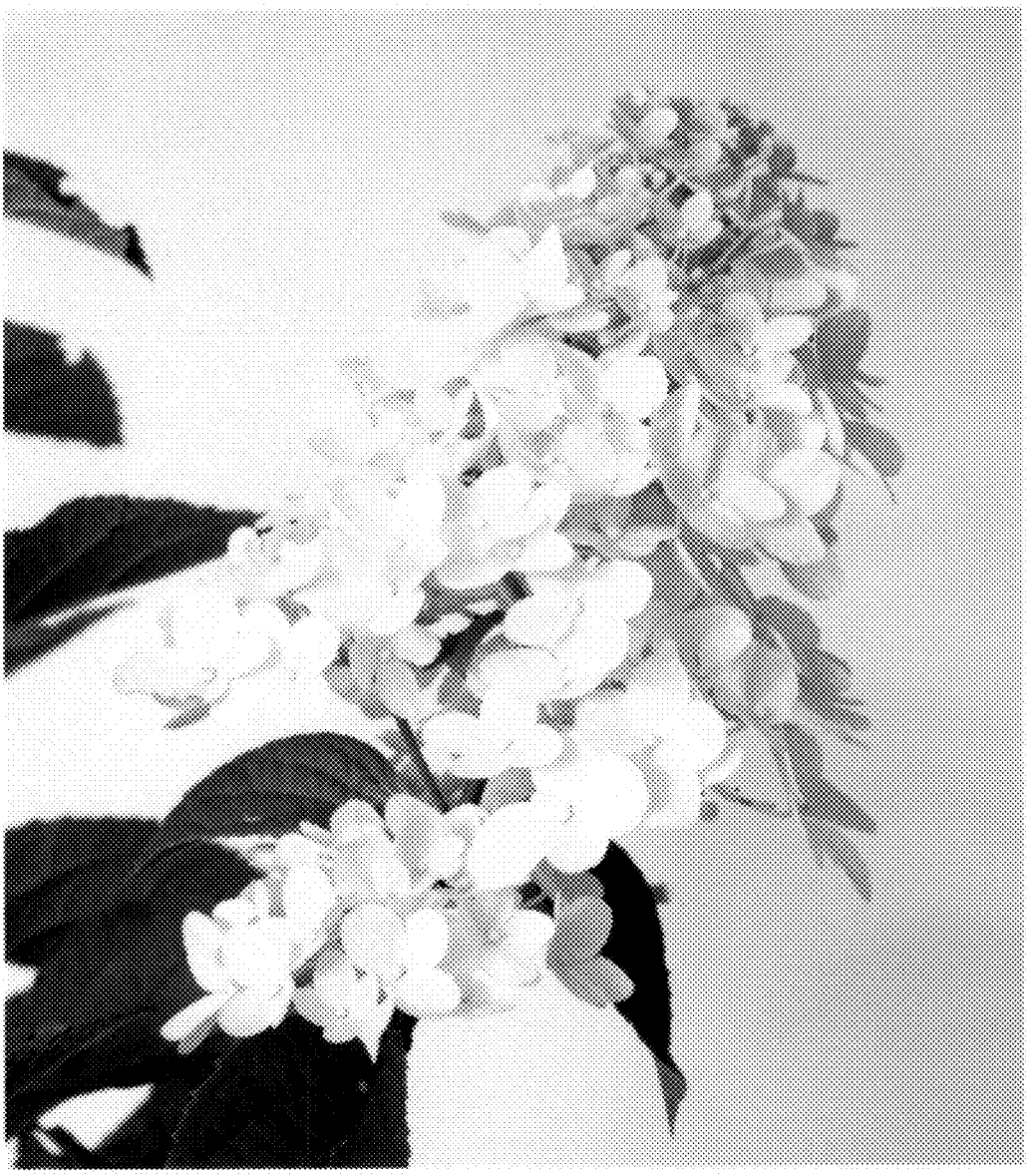

The photograph in FIG. 2 provides a close-up view of a newly opened inflorescence of 'Bokomabo'.

Figure 3:
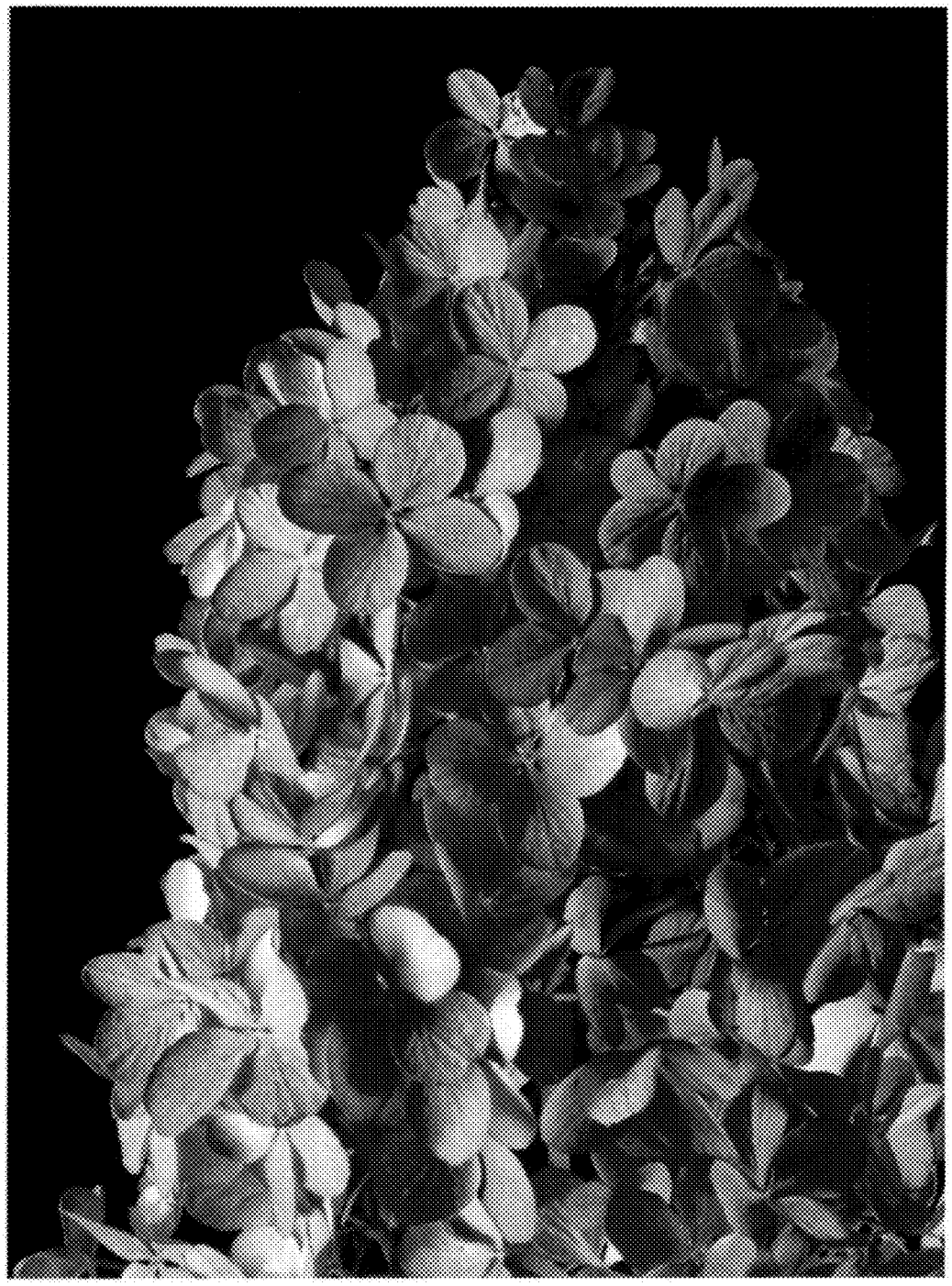

The photograph in FIG. 3 provides a close-up view of a maturing inflorescence of 'Bokomabo'.

Figure 4:
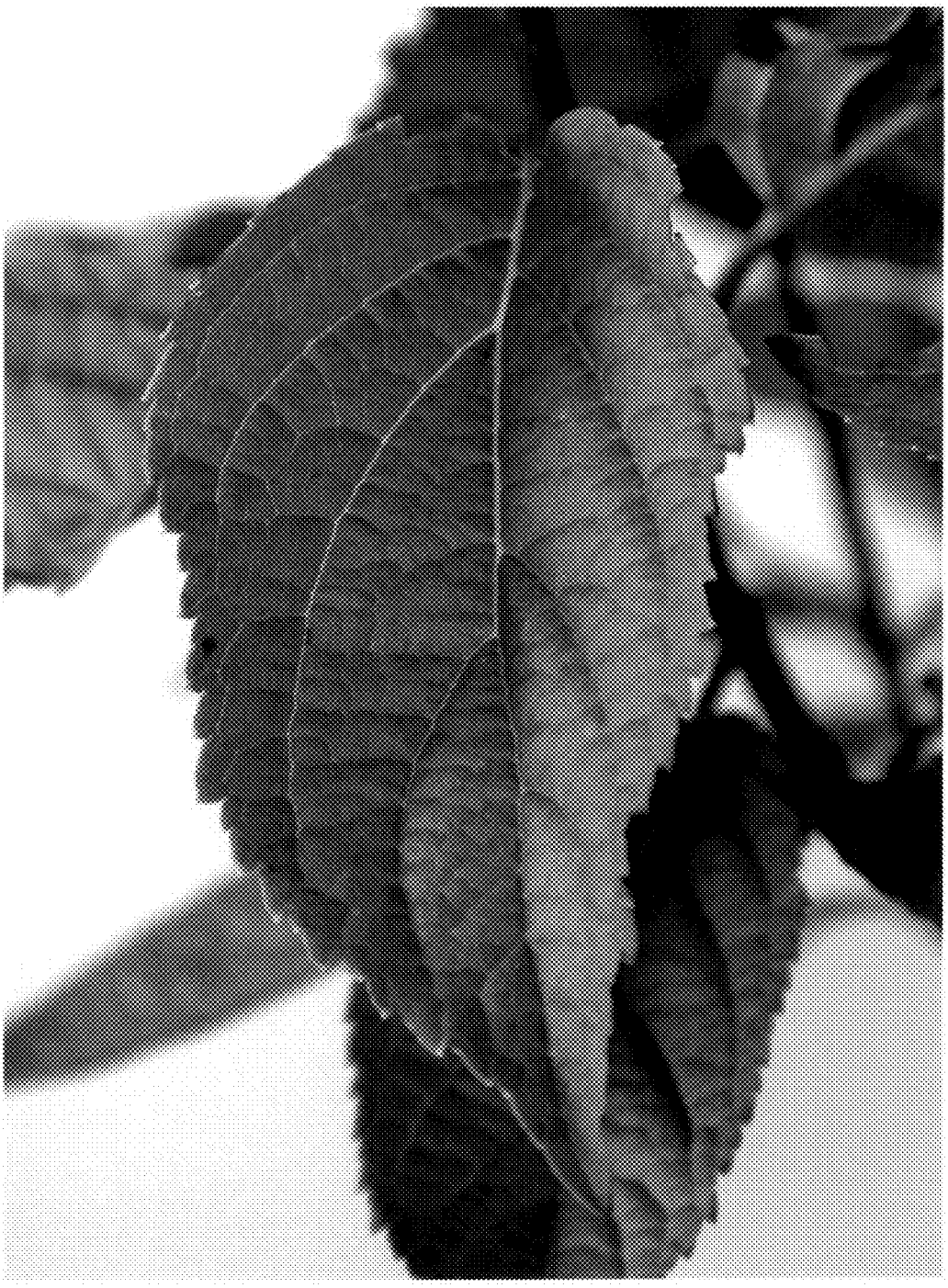

The photograph in FIG. 4 provides a close-up view of a leaf of 'Bokomabo'.

The colors in the photographs are as close as possible with the photographic and printing technology utilized and the color values cited in the detailed botanical description accurately describe the colors of the new *Hydrangea*.

BOTANICAL DESCRIPTION OF THE PLANT

The following is a detailed description of two-year-old plants of 'Bokomabo' as grown in 19-cm containers outdoors in Boskoop, The Netherlands. The phenotype of the new cultivar may vary with variations in environmental, climatic, and cultural conditions, as it has not been tested under all possible environmental conditions. The color determination is in accordance with The 2015 Colour Chart (2019 reprint) of The Royal Horticultural Society, London, England, except where general color terms of ordinary dictionary significance are used.

General description:

*Blooming period.*—8 weeks from early July into early fall in The Netherlands.

*Plant type.*—Deciduous shrub, panicle type *Hydrangea.*

*Plant habit.*—Compact, spreading, upright.

*Height and spread.*—An average of 69 cm in height and 52 cm in width as grown in a container and a 3-year-old plant matures in the landscape to 50 cm in height and 45 cm in width.

*Hardiness.*—At least in U.S.D.A. Zones 5 to 9.

*Diseases and pests.*—No susceptibility and resistance to diseases or pests has been observed.

*Root description.*—Fine, fibrous and dense, 161A in color.

*Propagation.*—Softwood stem cuttings.

*Root development.*—A young rooted plant is produced from a cutting in an average of 12 weeks.

*Growth rate and vigor.*—Moderate.

Branch description:

*Branch shape.*—Round.

*Branch strength.*—Strong.

*Branch color.*—Young; 185B, mature and older branches; N199C, older bark 200B, N200A, and N200B.

*Branch size.*—26.2 cm in length, 4.5 mm in diameter.

*Branch surface.*—Young; slightly glossy, sparsely to moderately covered with very short adpressed hairs; 0.5 mm in length, impossible to measure color due to small size and sparseness, mature; matte, moderately covered with round to linear shaped lenticels; an average of 0.5 mm in diameter, too small to measure color, mature; older wood and trunk; rugose, a blend of glossy and matte, base of truck slightly exfoliating.

*Branch aspect.*—Upright.

*Internode length.*—An average of 5.3 cm.

*Branching.*—Main; 1, lateral; 10.

Foliage description:

*Leaf shape.*—Ovate, slightly to moderately carinate.

*Leaf arrangement.*—Opposite, occasionally in whorls of 3.

*Leaf division.*—Simple.

*Leaf base.*—Obtuse to acute.

*Leaf apex.*—Apiculate.

*Leaf margins.*—Serrate.

*Leaf blade lobing.*—Shallow.

*Leaf venation.*—Pinnate, color; upper surface 148C, lower surface 195B.

*Leaf size.*—An average of 12.2 cm in length and 6.5 cm in width.

*Leaf attachment.*—Petiolate.

*Leaf number.*—An average of 10 (5 pairs) per lateral stem.

*Leaf surface.*—Both surfaces matte and sparsely pubescent.

*Leaf color.*—Young upper surface; 144A and 146B, young lower surface; 146C, mature upper surface; 144A, mature lower surface; a blend of 146B and 146C.

*Petioles.*—An average of 2.8 cm in length and 2.5 mm in width, both surfaces slightly glossy, sparsely covered with minute pubescent hairs 0.4 mm in length that match surface colors, color; upper surface 178A, lower surface 177A.

Inflorescence description:

*Inflorescence type.*—Terminal conical panicle, comprised of single sterile and fertile flowers.

*Lastingness of inflorescence.*—Sterile flowers; persistent for an average of 6 weeks, fertile flowers; self-cleaning, an average of 5 days.

*Inflorescence number.*—One per lateral stem.

*Inflorescence size.*—An average of 18 cm in height and 14.3 cm in diameter.

*Flower number.*—An average of 250 sterile flowers and 180 fertile flowers per panicle.

*Flower fragrance.*—None.

*Flower aspect.*—Sterile and fertile flowers; upright to outward.

*Flower size.*—Sterile flowers; (including showy sepals) up to 3.6 cm in diameter and 7 mm in depth, fertile flowers; an average of 1.4 cm in diameter and 8 mm in depth.

*Flower type.*—Rotate.

*Peduncles.*—Moderately strong, an average of 17 cm in length and 3 mm in width, color; 184A and 184B, surface is matte, densely covered with thin adpressed hairs 0.75 mm in length, N155A in color, main peduncle straight on top of lateral branch) (=0°), lateral peduncles in an average angle of 45° to main peduncle.

*Pedicels*.—Sterile flowers; moderate strength, an average of 2.1 cm in length and 1 mm in width, 157D in color, surface is matte and glabrous, moderately covered with pubescence 0.4 mm in length, matches surface colors, fertile flowers; moderately strong, held in an average angle of 5°, matte surface, an average of 2 mm in length, 1 mm in width, 155C in color.

*Petals*.—Sterile flowers: flower bud; 7 mm in depth, 1.3 cm in diameter, round in shape, 154D in color, when petals open; 4, occasionally 3 or 5, rotate, ovate and strongly concave in shape, acute apex, cuneate base, entire margins, 3 mm in length and 1.5 mm in width, both surfaces are glabrous, satiny, and slightly glossy, color; both surfaces when opening and fully open NN155C, petals drop after opening after maturity, fertile flowers: flower bud; 5 mm in depth, 3 mm in diameter, broad obovate in shape, color; 157C, immature calyx and ovary 192B and 192C, when petals open; 5, rotate, ovate to moderately concave in shape, acute apex, cuneate base, entire margins, 4 mm in length, 2 mm in width, both surfaces are glabrous, satiny, and slightly glossy, color; both surfaces when opening 155C, both surfaces when fully opening NN155D, petals drop after opening later in the season.

*Sepals*.—Sterile flowers; varies between 4 to 5 per flower, rotate, broadly ovate to broadly obovate, flat to very slightly concave in shape, apex is obtuse, base is cuneate, entire to shallowly and finely dentate-serrate margins, 1.7 cm in length, 1.4 cm in width, both surfaces glabrous, satiny, and matte, color: when opening upper surface; 155A, when opening lower surface; 155C, when fully open upper surface; NN155B, when fully open lower surface; 155B, maturing to fading; 63C, 63D, 185D and a blend of 63B and 184D, eventually fading to 184B, fertile flowers; average of 5, acute apex, broadly cuneate base, entire margins, 1 mm in length and width, surfaces are matte and glabrous, color; when opening upper and lower surface 192B and 192C, when fully open upper and lower surface 192B.

Reproductive organs:

*Gynoecium*.—Sterile flowers; not present, ovary; non-distinguishable, fertile flowers; 3 pistils, 1.5 mm in length, stigma; club-shaped and 155C in color, style; 0.15 mm in length, 157D in color, ovary is superior, 1 mm in depth and diameter, 157D in color.

*Androecium*.—Sterile flowers; 8 to 10 stamens, filaments; an average of 3 mm in length, 0.5 mm in diameter, NN155D in color, anthers; oblong in shape, an average of 0.5 mm in diameter, 155A in color, pollen; low, 161D in color, fertile flowers; an average of 10 stamens, filaments; an average of 6 mm in length, 0.5 mm in diameter, 155C in color, anthers; oblong in shape, an average of 0.5 mm in diameter, 155A in color, pollen; low, 161D in color.

*Fruit and seed*.—None observed to date.

It is claimed:

1. A new and distinct cultivar of *Hydrangea* plant named 'Bokomabo' substantially as herein illustrated and described.

* * * * *